US012728140B2

(12) United States Patent
Parthasarathy

(10) Patent No.: US 12,728,140 B2
(45) Date of Patent: Sep. 8, 2026

(54) TROJAN CIRCULATING TUMOR CELLS

(71) Applicant: Astrin Biosciences Inc., St. Paul, MN (US)

(72) Inventor: Jayant Parthasarathy, Excelsior, MN (US)

(73) Assignee: Astrin Biosciences, Inc., St. Paul, MN (US)

( * ) Notice: Subject to any disclaimer, the term of this patent is extended or adjusted under 35 U.S.C. 154(b) by 492 days.

(21) Appl. No.: 18/558,318

(22) PCT Filed: May 6, 2022

(86) PCT No.: PCT/US2022/028101
§ 371 (c)(1),
(2) Date: Oct. 31, 2023

(87) PCT Pub. No.: WO2022/236073
PCT Pub. Date: Nov. 10, 2022

(65) Prior Publication Data

US 2024/0226147 A1 Jul. 11, 2024

Related U.S. Application Data

(60) Provisional application No. 63/184,989, filed on May 6, 2021.

(51) Int. Cl.

| | |
|---|---|
| ***A61K 35/13*** | (2015.01) |
| ***A61K 40/19*** | (2025.01) |
| ***A61K 40/24*** | (2025.01) |
| ***A61K 40/42*** | (2025.01) |
| ***C12N 5/0784*** | (2010.01) |
| ***C12N 5/09*** | (2010.01) |
| ***G01N 33/50*** | (2006.01) |

(52) U.S. Cl.
CPC .............. *A61K 35/13* (2013.01); *A61K 40/19* (2025.01); *A61K 40/24* (2025.01); *A61K 40/428* (2025.01); *C12N 5/0639* (2013.01); *C12N 5/0693* (2013.01); *G01N 33/5011* (2013.01)

(58) Field of Classification Search
CPC ...................................................... A61K 35/13
See application file for complete search history.

(56) References Cited

U.S. PATENT DOCUMENTS

| | | | |
|---|---|---|---|
| 10,677,708 | B2 | 6/2020 | Nagrath et al. |
| 2013/0243820 | A1 | 9/2013 | Taylor et al. |
| 2019/0307868 | A1 | 10/2019 | Rooney |
| 2021/0069311 | A1 | 3/2021 | Sakuma et al. |

OTHER PUBLICATIONS

Nakamura et al. (Personalized Medicine Universe, vol. 8, 2019).*
PCT Application No. PCT/US2022/028101, International Preliminary Report on Patentability, dated Oct. 24, 2023.
Hughes et al., Differential Drug Responses of Circulating Tumor Cells within Patient Blood, Cancer Lett., Sep. 28, 2014; vol. 352(1), pp. 28-35.
Samuel et al., Personalized Medicine and Back-Allogeneic Exosomes for Cancer Immunotherapy, Journal of Internal Medicine, Jul. 29, 2019, vol. 289, pp. 138-146.

* cited by examiner

*Primary Examiner* — Gary B Nickol
(74) *Attorney, Agent, or Firm* — Lisa Hillman; Lathrop GPM LLP

(57) ABSTRACT

Provided herein are compositions and methods for engineering treatment resistant circulating tumor cells to generate immune stimulating or anti-cancer exosomes, which can be infused into a patient to self-home to the primary tumor and metastatic lesions. Also provided are compositions and methods for forming a population of engineered exosome-loaded dendritic cells, which can be infused into the patient to activate a systemic immune response. The compositions and methods allow for infiltration into solid tumors using "trojan" cells that are naturally adapted and mechanistically engineered to evade patients' defenses.

20 Claims, 1 Drawing Sheet

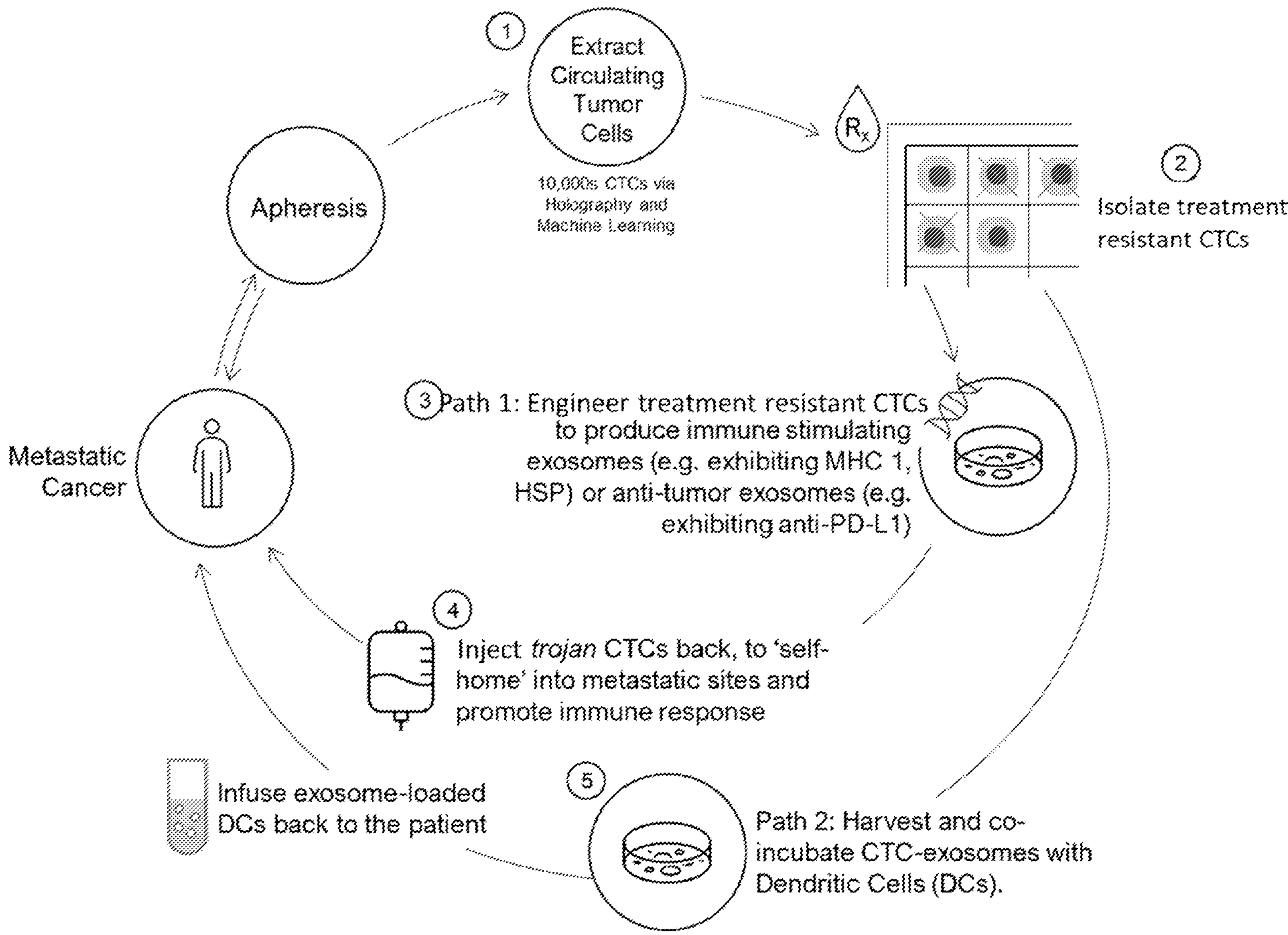
1
Extract Circulating Tumor Cells
10,000s CTCs via Holography and Machine Learning
Rx
2
Isolate treatment resistant CTCs
Apheresis
Metastatic Cancer
3
Path 1: Engineer treatment resistant CTCs to produce immune stimulating exosomes (e.g. exhibiting MHC 1, HSP) or anti-tumor exosomes (e.g. exhibiting anti-PD-L1)
4
Inject *trojan* CTCs back, to 'self-home' into metastatic sites and promote immune response
Infuse exosome-loaded DCs back to the patient
5
Path 2: Harvest and co-incubate CTC-exosomes with Dendritic Cells (DCs).

TROJAN CIRCULATING TUMOR CELLS

PRIORITY

This application claims the benefit of U.S. Provisional Patent No. 63/184,989, filed on May 6, 2021, which is incorporated by reference in its entirety herein.

BACKGROUND

Immunotherapy, the most recent addition to the pillars of cancer treatment, shows great promise in addressing a number of treatment challenges and improving patients' lives. Despite advancements, immunotherapy has come up against challenges in addressing solid tumors, primarily due to the tumor micro-environment acting as a defense mechanism. These defense mechanisms vary based on the specific cancer type and other factors, but may involve strategies such as immunosuppression at the CTLA-4 and PD-1 checkpoints for T cells, CD38 enzymatic activity, and Galectin-1 (Gal-1) overexpression. Methods are needed in the art to bypass these defenses.

SUMMARY

Provided herein are methods of treating a cancer patient that can include: (a) extracting circulating tumor cells from the cancer patient to produce a population of isolated circulating tumor cells; (b) isolating a population of treatment resistant circulating tumor cells from the population of isolated circulating tumor cells; (c) genetically engineering the treatment resistant circulating tumor cells to generate immune stimulating or anti-cancer exosomes to produce a population of genetically engineered treatment resistant circulating tumor cells; (d) administering the genetically engineered treatment resistant circulating tumor cells to the cancer patient.

In some embodiments, the method can further include, either sequentially or simultaneously, (a) harvesting exosomes from the population of treatment resistant circulating tumor cells to produce a population of isolated treatment resistant circulating tumor cell exosomes; (b) incubating the population of isolated treatment resistant circulating tumor cell exosomes with dendritic cells to form a population of exosome-loaded dendritic cells; and (c) administering the population of exosome-loaded dendritic cells to the cancer patient. In some embodiments, the population of isolated circulating tumor cells can be extracted from a biological fluid, a fragmented tumor, a tumor suspension, a tissue suspension, a cell culture, an established cell line, or combinations thereof. In some embodiments, extracting circulating tumor cells can further include using a biological fluid filtration system, immunomagnetic separation, a system for identification and enumeration of circulating tumor cells from blood, immunoaffinity purification using antibodies, capture using aptamers, nanostructured surfaces for capture, size-based filtration, microfluidic separation, dielectrophoresis-based separation, or combinations thereof. In some embodiments, the population of isolated circulating tumor cells can be greater than about 1,000 cells. In some embodiments, isolating the population of treatment resistant circulating tumor cells from the population of isolated circulating tumor cells further can further include: exposing the population of isolated circulating tumor cells to anti-cancer agents for 1, 2, 3, 4, 5, 6, 7, or 8 days; and measuring cell viability and or cell survival. In some embodiments, the population of treatment resistant circulating tumor cells can be isolated from the population of circulating tumor cells when one or more anti-cancer agents inhibit tumor cell growth, decrease cell viability, and/or decrease cell survival by about 50% or more when compared to a tumor cell whose growth, viability, and/or cell survival is inhibited or destroyed by one or more anti-cancer agents. In some embodiments, the population of treatment resistant circulating tumor cells can include circulating tumor cells that are chemo-resistive, targeted therapy resistive, immunotherapy resistive, or cells resistant to combinations of treatments.

Also provided herein are methods of treating a cancer patient that can include: (a) extracting circulating tumor cells from a cancer patient to produce a population of isolated circulating tumor cells; (b) isolating a population of treatment resistant circulating tumor cells from the population of isolated circulating tumor cells; (c) harvesting exosomes from the population of isolated treatment resistant circulating tumor cells to produce a population of isolated treatment resistant circulating tumor cell exosomes; (d) incubating the population of isolated treatment resistant circulating tumor cell exosomes with dendritic cells to form a population of exosome-loaded dendritic cells; and (e) administering the population of exosome-loaded dendritic cells to a cancer patient in need thereof.

In some embodiments, the method can further include: (f) genetically engineering the treatment resistant circulating tumor cells to generate immune stimulating or anti-cancer exosomes to produce a population of genetically engineered treatment resistant circulating tumor cells; and (g) the genetically engineered treatment resistant circulating tumor cells into the cancer patient in need thereof. In some embodiments, (g) administering the genetically engineered treatment resistant circulating tumor cells to the cancer patient can occur simultaneously with (e) administering the population of exosome-loaded dendritic cells to the cancer patient in need thereof. In some embodiments, (g) administering the genetically engineered treatment resistant circulating tumor cells to the cancer patient can occur prior to (e) administering the population of exosome-loaded dendritic cells to the cancer patient in need thereof. In some embodiments, (g) administering the genetically engineered treatment resistant circulating tumor cells to the cancer patient can occur after (e) administering the population of exosome-loaded dendritic cells to the cancer patient in need thereof.

Therefore, provided herein are compositions and methods for technology that allows for infiltration into solid tumors using "trojan" cells that are naturally adapted and mechanistically engineered to evade patients' defenses.

BRIEF DESCRIPTION OF THE DRAWINGS

Various objectives, features, and advantages of the disclosed subject matter can be more fully appreciated with reference to the following detailed description of the disclosed subject matter when considered in connection with the following drawings, in which like reference numerals identify like elements.

FIG. 1 shows an exemplary method for treating cancer in a patient by extracting and isolating treatment resistant (e.g., chemo-resistive) circulating tumor cells (CTCs). Path 1 proceeds by engineering treatment resistant (e.g., chemo-resistive) CTCs to produce immune stimulating or anti-cancer exosomes and then administering treatment resistant "trojan" CTCs back to the patient to promote a local immune response. Path 2 proceeds by harvesting and co-incubating CTC-exosomes with dendritic cells (DCs) and then by administering exosome-loaded DCs back to the patient to promote a systemic immune response.

The drawings are not necessarily to scale, or inclusive of all elements of a system, emphasis instead generally being placed upon illustrating the concepts, structures, and techniques sought to be protected herein.

DETAILED DESCRIPTION

The details of one or more variations of the subject matter described herein are set forth in the accompanying drawings and the description below, Other features and advantages of the subject matter described herein will be apparent from the description and drawings, and from the claims. The disclosed subject matter is not, however, limited to any particular embodiment disclosed.

Circulating Tumor Cells (CTCs)

Circulating tumor cells (CTCs) are cells originating from a primary tumor that can be found in the bloodstream. Though heterogeneous in their genomic and molecular make-up, some CTCs possess tumor-initiating capacities and thus act as effective metastasizing agents. CTCs and CTC clusters are negative predictors of disease outcomes. Surgical excision of primary tumors can release CTCs, and increased levels of CTCs are associated with relapse or further metastasis. CTCs are unique in their ability to return to the original tumor, which is called self-homing, or when they contribute to proliferation of the primary tumor, self-seeding. Over the last two decades, various groups have tried to exploit the self-homing capacity of CTCs. These studies, however, have shown limited capacity due to the paucity of CTC cells that can be extracted from a patient and limitations in enrichment, isolation, and identification of CTCs resulting in low purity, low cell viability, and low intermediate throughput.

Accordingly, embodiments of the present disclosure provide compositions and methods for isolating large volumes of CTCs, engineering the CTCs ex vivo to produce immune-stimulating exosomes, and returning the CTCs to the bloodstream where they mobilize to primary and developing lesions, thereby acting as a beacon to stimulate a swift, localized immune response. A systemic response can be also induced by infusing the patient with immune cells sensitized by treatment resistant (e.g., chemo-resistant), CTC-derived exosomes.

In some embodiments, methods of treating cancer patients are provided. The methods can comprise extracting circulating tumor cells from a cancer patient to produce a population of isolated circulating tumor cells. From these isolated circulating tumor cells, a population of treatment resistant circulating tumor cells can be isolated. The treatment resistant circulating tumor cells can be genetically engineered to generate immune stimulating or anti-cancer exosomes to produce a population of genetically engineered treatment resistant circulating tumor cells. The genetically engineered treatment resistant circulating tumor cells can be administering to the cancer patient. The methods can further comprise harvesting exosomes from the population of treatment resistant circulating tumor cells to produce a population of isolated treatment resistant circulating tumor cell exosomes and incubating these exosomes with dendritic cells to form a population of exosome-loaded dendritic cells. The population of exosome-loaded dendritic cells can be administering to the cancer patient.

Methods of Collecting CTCs in Patients

Circulating tumor cells (CTCs) are a subset of cells found in the blood of patients with solid tumors. CTCs refer to a small number of cells that are shed into the bloodstream from both primary and metastatic lesions. CTCs are thought to be responsible for the hematogenous spread of cancer to distant sites. Cancer cells metastasize through the bloodstream either as single migratory CTCs or as multicellular groupings called CTC clusters. CTC clusters can range from two or more cells to clusters of more than 70 cells (e.g., about 2, 5, 10, 20, 30, 40, 50, 60, 70 or more cells). The CTCs preserve primary tumor heterogeneity and mimic tumor properties and can be considered as clinical biomarker, preclinical model, and therapeutic target.

Circulating tumor cells from a cancer patient can be isolated using any known method. In some embodiments, methods are used that can isolate 500 or more (e.g., about 500, 1,000, 2,000, 3,000, 4,000, 5,000, 10,000, or more) CTCs and CTC clusters from a patient in a single collection session.

CTC cells can be kidney cancer cells such as clear cell kidney cells, papillary kidney cells, medullary collecting duct kidney cells, chromophobe kidney cells, oncocytoma kidney cells, or angiomyolipoma kidney cells. In an embodiment the cancerous cells are bladder cancer cells, breast cancer cells, colon cancer cells, rectal cancer cells, endometrial cancer cells, leukemia cells, liver cancer cells, lung cancer cells (e.g., non-small cell lung cancer cells, small cell lung cancer cells), melanoma cells, non-Hodgkin lymphoma cells, pancreatic cancer cells, prostate cancer cells, thyroid cancer cells, parathyroid cancer cells, neuroblastoma cancer cells, lymphoma cancer cells, adrenocortical cancer cells, sarcoma cells, bile duct cancer cells, brain cancer cells, bone cancer cells, gastrointestinal cancer cells, cardiac cancer cells, cervical cancer cells, chronic myeloproliferative neoplasm cells, esophageal cancer cells, head and neck cancer cells, retinoblastoma cells, gall bladder cancer cells, testicular cancer cells, ovarian cancer cells, laryngeal cancer cells, or any other suitable cancer cells.

CTCs can be isolated from biological fluid such as whole blood, plasma, serum, any cell-containing blood fraction, a fragmented tumor, a tumor cell suspension, a tissue suspension, or a cell culture established from a patient's sample, the culture supernatant, or the like. In some embodiments, CTCs can be isolated from an established cell line culture or culture supernatant or from an experimental animal, e.g. from an animal carrying a xenograft tumor.

Methods of extracting CTCs can include, for example, using a biological fluid filtration system, immunomagnetic separation, a CellSearch® system (Janssen Diagnostics; South Raritan, N.J. (USA)), immunoaffinity purification of CTCs using antibodies, capture of CTC using aptamers, nanostructured surfaces for CTC capture, size-based filtration, microfluidic separation (see, e.g., U.S. Pat. No. 10,677,708), dielectrophoresis-based separation, or other suitable method.

Methods of extracting CTCs can include a biological fluid filtration system, for example, a high through-put holography and machine learning method to isolate large numbers of CTCs from cancer patients via leukapheresis extracts. A biological fluid filtration system can comprise a fluid receiving device to receive a biological fluid; a valve fluidly connected to the fluid receiving device; a scanner configured to scan the biological fluid within the fluid receiving device to produce a scanned data relating to the biological fluid within the fluid receiving device; and a control unit in communication with the scanner and the valve. In some embodiments, the control unit can be configured to receive the scanned data from the scanner, and wherein the control unit can be configured to control the valve based on the scanned data from the scanner. The control unit can be configured to control the valve to (a) direct the biological fluid through the first outlet if the control unit determines that the scanned data indicates a presence of CTC, CTCs, or a CTC-cluster within the biological fluid or (b) direct the biological fluid through the second outlet if the control unit determines that the scanned data does not indicate a presence of CTC, CTCs, or a CTC-cluster within the biological fluid. In some embodiments, the fluid receiving device can be a microfluidic channel.

A wide range of scanning techniques can be utilized to scan the biological fluid and identify any constituent biological elements thereof, such as but not limited to CTCs. Exemplary techniques for scanning can include Phase contrast microscopy (PCM), DIC Microscopy, Hoffman modulation, polarized light microscopy, digital holographic microscopy (DHM), confocal scanning optic microscopy (CSOM), or laser scanning optic microscopy (SOM) to measure voxel fluorescence, bright-field microscopy, dark-field illumination, Raman spectrometry to measure Raman Scattering, Optical interferometry to measure optical interference, total internal reflection fluorescence microscopy to measure evanescent effect, planar waveguides for refractive index detection, photonic crystal biosensors for measure of biomolecules on cell surfaces, and light property modulation detections such as surface plasmon resonance (SPR) detection.

With respect to digital holographic microscopy, digital holography is used to record a wave front diffracted from an object by a light source. Utilizing the interference of light from the light source, both amplitude and phase information of an object wave can be recorded to produce a hologram containing the information of the object wave. A three-dimensional image can then be reconstructed from the hologram by the control unit.

While a microscope objective can be used to collect the object wave front, it should be appreciated that the microscope objective is only used to collect light waves and not to form an image. Thus, the microscope objective can comprise a simple lens, or can be omitted entirely. The interference pattern (hologram) can thus be recorded in such embodiments by a digital image sensor. Digital holographic microscopy can be utilized to observe living cells within the biological fluid. From the recorded interference pattern of such living cells, the intensity and phase shift across various points of the cells can be numerically computed by the control unit. The control unit can thus measure the phase delay images of biological cells within the biological fluid to provide quantitative information about the morphological properties (e.g., cellular dry mass, surface texture, shape, etc.) of individual cells within the biological fluid.

In some embodiments, the systems and methods of biological fluid filtration described herein can utilize these quantitative indicators of morphological properties in an algorithm to distinguish between cell types within the biological fluid. By way of example and without limitation, the control unit can be adapted to extract parameters such as cell thickness, cell area, cell volume, cell dry mass, the phase shift across the cell, surface roughness and texture, cell shape, elongation, convexity, luminance, circularity, solidity, and the like. Various types of digital holography can be utilized with the systems and methods described herein, including but not limited to off-axis Fresnel, Fourier, image plane, in-line, Gabor, and phase-shifting digital holography. By utilizing digital holographic microscopy, the control unit can differentiate between the various constituents within a biological fluid sample for further processing utilizing the systems and methods described herein.

Multiple laser wavelengths can be utilized when scanning the biological fluid with digital holographic microscopy. The refraction amount increases as the wavelength of light decreases. Thus, shorter wavelengths of light (e.g., violet and blue) are more slowed and consequently experience more bending than longer wavelengths of light (e.g., orange and red). Since the morphological parameters in digital holographic microscopy are dependent upon the wavelength of the laser used, some embodiments of a scanning technique relying upon digital holographic microscopy can utilize multiple lasers each having different wavelengths. By way of example, the analysis can be initially conducted using a light source at a first wavelength. If the sample of cells requires additional confirmation, the light source may be switched to a different wavelength.

Methods of biological fluid filtration can involve directing a biological fluid to a fluid receiving device, optically scanning the biological fluid within the fluid receiving device by a scanner to generate the scanned data of the biological fluid, comparing the scanned data of the biological fluid with the reference data by the control unit; returning the biological fluid to the biological fluid source if the scanned data of the biological fluid includes only desirable constituents exhibiting criteria that sufficiently match with any of the desirable constituents of the reference data by the control unit; and isolating the biological fluid from the biological fluid source if the scanned data of the biological fluid includes one or more constituents not exhibiting criteria that sufficiently match with any of the desirable constituents of the reference data by the control unit.

The methods can include pre-processing of a fluid sample of the biological fluid source to obtain the reference data differentiating cell image data characteristics of desirable constituents to more precisely tailor the reference data the biological fluid system, including any heterogeneity among its desirable constituents. Such pre-processing can rely upon machine learning and/or artificial intelligence models in order to more accurately and efficiently differentiate between undesirable constituents and desirable constituents.

Reference data can be developed based on relevant normative subpopulation data concerning the desirable constituents of the biological fluid system.

In some embodiments, blood comprised of a leukapheresis product can be collected from a patient. Pre-sorting can be performed by a microfluidic separation module so as to separate the leukapheresis product into three primary divisions: (1) separated red blood cells, plasma, and small cells; (2) separated white blood cells and small CTCs; and (3) separated large CTC-clusters. In some embodiments, pre-sorting can involve the use of chemical agents and/or buffer solutions for red blood cell and platelet separation or lysis.

The first division, comprised of separated red blood cells, plasma, and small cells, can be transferred to a fluid chamber to hold filtered plasma and healthy cells for transplantation. The third division, comprised of large CTC-clusters, can be transferred for diagnostic processing (e.g., genomic, transcriptomic, metabolomics, drug sensitivity and resistance) of CTCs, CTC-clusters, and cell-free plasma.

With respect to the second division, comprised of separated white blood cells and small CTCs, such contents can be inertial focused into one or more parallel fluid receiving devices (e.g., microfluidic channels, microwell arrays, and/or droplet generators). Such contents can be scanned simultaneously or sequentially by the scanner. The control unit can then analyze each sample to determine if cells other than healthy cells are present such as CTCs and CTC clusters.

If no cells other than healthy cells are present in a given sample, that sample can be transferred to a fluid chamber along with the first division of separated red blood cells, plasma, and small cells. If cells other than healthy cells are present in a given sample, that sample can be further enriched (e.g., by returning to be reprocessed by a reprocessing path) or can be sequestered along with the third division of separated large CTC-clusters for diagnostic processing.

The methods can be used for aphaeretic scanning and filtration of Leukocyte-Rich Blood Fluid to remove CTCs from a patient's circulatory system. Leukocyte-Rich Blood Fluid is a type of platelet-rich plasma (PRP) defined as having a neutrophil concentration above baseline. In this example, whole blood is pumped from the patient into a receiver path that directs flow of the whole blood to a microfluidic separation module, which pre-sorts whole blood using appropriate sorting techniques, e.g., Dean flow fractionation or dielectric sorting, into three components: (1) fluid containing primarily healthy erythrocytes (RBCs) and platelets, (2) fluid largely containing a mixture of leukocytes (WBCs) and small CTCs, and (3) fluid containing large CTCs and CTC-clusters. The fluid containing a mixture of leukocytes and CTCs are promoted to fluid receiving device comprising a batch of parallel microfluidic channels. Each channel is optically scanned using DIC Microscopy, DHM, or other appropriate imaging techniques to derive a scanned data of the cells for each microfluidic channel.

The scanned data can be transferred to a control unit, which follows an image processing software program comprising an algorithm designed to recognize healthy blood cells in the scanned data. More particularly, the algorithm is designed to recognize a pattern in a reference data characteristic of healthy blood cells and process each scanned data transferred to the control unit to determine whether that pattern is recognized in discreet image data obtained for each cell (see, e.g., U.S. Patent App. No. 63/229,175). In the example, the reference data is obtained through DIC Microscopy or DHM of blood samples taken from a representative sample of individuals other than the patient. If all cells in a scanned microfluidic channel are recognized by the algorithm as healthy blood cells, then the image processing software program generates a first control signal instruction to the control unit to relay a control signal to the valve to route channel contents to the return path. If, on the other hand, one or more of cells of the scanned microfluidic channel are not recognized by the algorithm, then the image processing software program generates a second control signal instruction to the control unit to relay a control signal to the valve to route channel contents to the isolation path. Leukocytes routed to the return path are then recombined with the pre-sorted RBCs, plasma and platelets and pumped back to the patient's circulatory system. CTC-rich fluid routed to the isolation path is sequestered and optionally stored for further processing for therapeutic purposes according to embodiments of the present disclosure.

The systems and methods of biological fluid filtration described herein can be an optofluidic device capable of aphaeretic removal of CTCs from the blood stream. Using centrifugal enrichment of peripheral blood mononuclear cells, the approximately hour-long procedure extracts a leukapheresis product approximately 250 mL in volume. In some embodiments, the procedure can take 15, 20, 25, 30, 35, 40, 45, 50, 55, 60, 65, 70, 75, 80, 85, or 90 minutes. In some embodiments, the procedure can extract leukapheresis product approximately 50, 100, 150, 200, 250, 300, or 350 mL in volume. In some embodiments, the remaining constituents of the blood, including plasma, red blood cells (RBCs), and most neutrophils can be returned to the patient. Since CTCs have a similar density as mononuclear cells, they can be enriched in the leukapheresis product. Therefore, the platform can yield impressive volumes of >10,000 CTCs per procedure; this can allow for collection of a sufficient volume of CTCs for genetic engineering to take place, and for the identification of treatment resistant CTCs from which exosomes will be extracted.

About 500, 1,000, 2,000, 3,000, 4,000, 5,000, 6,000, 7,000, 8,000, 9,000, 10,000, 15,000, 20,000, or more CTCs can be isolated from a single patient in one round of isolation.

Other methods of extracting CTCs can include immunomagnetic separation. Pre-treated blood, like EDTA-treated blood from patients, can be subjected to a density-gradient centrifugation for the preliminary enrichment of target cells. After that, cells can be mixed with microbeads modified with antibody and can be incubated, during which time the cells can specifically bind to the antibody-modified microbeads. Target cells can be harvested by drawing cell-attached microbeads to the surface of steel wool fibers, which can induce a magnetic field. Traditional immunomagnetic separation can be effective for capturing target cells with good specificity by combining the use of a size-based density gradient and cell affinity. By taking advantage of the magnetic field, captured cells can be readily released. However, traditional immunomagnetic separation requires laborious operating steps and a long time, which may result in the loss of target cells during repeated pipetting and centrifugation steps, and changes to the cell properties over the several-hour operation.

In some embodiments, the CellSearch® system (system for identification, isolation, and enumeration of circulating tumor cells (CTCs) from blood; Janssen Diagnostics; South Raritan, N.J. (USA)) can be used. In the CellSearch® system, anti-EpCAM-coated ferrofluid nanoparticles retain CTCs upon passing through a magnetic field. The retained CTCs can be subjected to an immunostaining process, which distinguishes the CTCs from leukocytes, enabling the observation of the differences in cell size and morphology between CTCs and normal cells. CellSearch® can achieve an average recovery rate of blood samples spiked with defined numbers of carcinoma cells of no less than 80%, and the final results would not be influenced by storage or shipment within at least 72 h. Multiple challenges and manual labor are required to achieve a high purity for the enumeration.

In some embodiments, methods of extracting CTCs can include immunoaffinity purification of CTCs using antibodies. Epithelial cell adhesion molecule (EpCAM), for example, is a glycoprotein employed as a surface marker for CTC detection. Alternatively, prostate-specific membrane antigen (PSMA), a transmembrane metallopeptidase which can be used for the isolation of prostate cancer cells from peripheral blood. In addition to these positive isolation methodologies—the isolation methodologies using epitopes expressed on the target CTCs-negative isolation methodologies can also be used. Negative isolation methodologies can be based on the removal of nontarget cells, often involving the use of antibody targets to leukocyte surface marker CD45, which is not expressed on the surface of CTCs. By functionalizing devices with anti-CD45, the large abundance of leukocytes can be largely removed from blood while CTCs can be enriched and collected.

In some embodiments, methods of extracting CTCs can include capture of CTC using aptamers. Aptamers are oligonucleotides such as RNA, DNA, or certain peptides that can specifically bind to not only proteins but ions or small molecules that antibodies cannot recognize. An in vitro selection protocol for aptamers such as a three-step-based systematic evolution of ligands by exponential enrichment (SELEX) can be used. An aptamer-coated microfluidic chip can be used for CTC enrichment. In some embodiments, magnetic nanoparticles can be compatible carriers for aptamers as aptamers can readily self-assemble onto nanoparticles synthesized with a variety of functional groups. Combining magnetic nanoparticles and aptamers, Au nanoparticles functionalized with aptamers can be synthesized and successfully applied to the isolation of CTCs.

Methods of extracting CTCs can include nanostructured surfaces for CTC capture. Because an extracellular matrix (ECM) contains nanoscale components affecting cell functions, the structures formed by the ECM provide ways to fabricate artificial nanostructures that mimic the natural nanostructure of ECMs. Nanostructure-based methods can modify nanostructured surfaces with antibodies or aptamers. See U.S. Pat. No. 9,733,250 and CN Pat. No. 106148315. In some embodiments, CTCs can be isolated by nanostructured surface without functionalization.

Methods of extracting CTCs can also include filtration-based separation. Size-based separation methods can take advantage of the fact that CTCs have a larger size than blood cells. Separating larger tumor cells through filtering membranes can be a representative method independent of specific binding to antigens and can enable the separation of CTCs without knowing the specific surface markers of all CTC types. In some embodiments, an ISET (isolation by size of epithelial tumor cells) assay can be used. An ISET assay allows the counting and the immunomorphological and molecular characterization of circulating tumor cells using peripheral blood sample volumes as small as 1 ml. Using this assay, epithelial tumor cells can be isolated individually by filtration because of their larger size when compared to peripheral blood leukocytes. Apart from membrane-based filtration, techniques to equip microchannels with gradient widths to trap larger CTCs can also be used.

In other examples, methods of extracting CTCs can include dielectophoresis-based separation. Dielectrophoresis (DEP) is the transport of polarizable particles in response to an externally applied electric field. Some particle separation devices comprise planar microelectrode arrays such as interdigitated, polynomial and castellated microelectrodes embedded in microfluidic channels. They are used to separate particles using individual or a combination of positive and negative dielectrophoresis (voltage and frequency dependent). In some embodiments, the microchannels of microelectrode arrays with different geometries can be used to form nonuniform electric fields. Actuation is achieved by application of a nonuniform electric field which simultaneously induces polarization and exerts force on the interface between two electrically dissimilar media. In addition to the physical properties like cell size, electrical properties, which depend on the cellular composition, cell membrane, as well as cell size, are intrinsic properties of cells that can be used to differentiate CTCs from normal blood cells. By inserting external nonuniform electrical fields around the flow path through which the cell suspension flows, separation of CTCs can be realized due to the different polarization-induced dielectric forces exerted on cells. The release of captured CTCs can be implemented by withdrawing the external electrical field, which can be helpful for following bioanalysis. DEP-based CTC separation involves developing optimal electric field-induced devices based on the different responses to electric fields from cells.

Any of the above methods or any other suitable method can be used to extract circulating tumor cells from a cancer patient to produce a population of isolated circulating tumor cells.

Isolating Treatment Resistant Circulating Tumor Cells

Treatment resistant circulating tumor cells (CTCs) can be, for example, chemo-resistive, targeted therapy resistive, immunotherapy resistive, or cells resistant to combinations of treatments. Targeted therapies can include monoclonal antibodies, kinase inhibitors, cancer growth blockers, PARP inhibitors, signal transduction inhibitors, gene expression modulators, small molecule medicines, or combinations thereof. Immunotherapy therapies can include an interleukin, a cytokine, a chemokine, an immunomodulatory imide drug, CAR-T cells, TCR therapy, a monoclonal antibody, a cancer vaccine, a checkpoint inhibitor, or combinations thereof. Treatment-resistant circulating tumor cells can be isolated from a population of circulating tumor cells. Increased efflux of drug, enhanced repair/increased tolerance to DNA damage, high antiapoptotic potential, decreased permeability, and/or enzymatic deactivation can allow a tumor cell to survive treatment with one or more classes of anti-cancer agents. Methods of isolating treatment resistant circulating tumor cells include use of drug response assays (e.g., chemoresistance test). For example, an ex vivo drug test can be performed with a population of CTCs to isolate those that are resistant or partially resistant to anti-cancer (e.g., chemotherapeutic) agents.

In an example, a drug response assay can be used to identify treatment resistant circulating tumor cells. The isolated CTCs can be kept under conditions that favor growth of tumor cells and that suppress growth of possibly interfering non-CTC or contaminating cells. The CTCs can then be exposed to different anti-cancer agents for, for example, 1, 2, 3, 4, 5, 6, 7 or more days. In some embodiments, the CTCs can be exposed to any one or combination of the cancer treatments disclosed herein Cell viability and survival can be evaluated by, for example, measuring ATP using commercially available reagents such as CellTiter-Glo (Promega, Madison, WI). Other methods include, for example adding tritium-labeled thymidine to cells during the last 1, 2, 3, or 4 days to enable determination of cell growth. CTCs will have grown at differing strengths (e.g., extreme cell growth, medium cell growth, or slight cell growth). Labeled genomic DNA is extracted from the cells and the activity of labeled DNA is read by, e.g., a scintillation counter, and cell growth is calculated. The growth of cells treated with chemotherapeutic agent(s) is compared to the growth of an untreated control group. In this case cells exposed to a chemotherapeutic agent and exhibiting resistance (e.g., extreme cell growth and/or medium cell growth) are selected as chemo-resistive circulating tumor cells.

In an embodiment a tumor cell is treatment resistant when one or more anti-cancer agents inhibit tumor cell growth, decrease cell viability, and/or decrease cell survival by about 50, 40, 30, 40, 30, 20, 10, 5, 1% or less when compared to a tumor cell whose growth, viability, and/or cell survival is completely inhibited or destroyed by one or more anti-cancer agents.

Anti-cancer agents can include, anti-cancer drugs anti-cancer or therapies, for example, alkylating agents, anthracyclines, cytoskeletal disruptors (taxanes), epothilones, histone deacetylase inhibitors, inhibitors of topoisomerase I and II, kinase inhibitors, nucleotide analogs and precursor analogs, peptide antibiotics, platinum-based agents, retinoids, vinca alkaloids and derivatives, any other chemotherapeutic agent, or combinations thereof. Alkylating agents can include bifunctional alkylators, such as Cyclophosphamide, Mechlorethamine, Chlorambucil, or Melphalan, and monofunctional alkylators, such as Dacarbazine, Nitrosoureas, or Temozolomide. Anthracyclines can include daunorubicin, Doxorubicin, Epirubicin, Idarubicin, Mitoxantrone, or Valrubicin. Cytoskeletal disruptors (taxanes) can include Paclitaxel, Docetaxel, Abraxane, or Taxotere. Epothilones can include, for example, Epothilone B, or Epothilone D. Histone deacetylase inhibitors can include Vorinostat or Romidepsin. Inhibitors of topoisomerase I can include Irinotecan or Topotecan. Inhibitors of topoisomerase 11 can include Etoposide, Teniposide, or Tafluposide. Kinase inhibitors can include Bortezomib, Erlotinib, Gefitinib, Imatinib, Vemurafenib, or Vismodegib. Nucleotide analogs and precursor analogs can include Azacitidine, Azathioprine, Capecitabine, Cytarabine, Doxifluridine, Fluorouracil, Gemcitabine, Hydroxyurea, Mercaptopurine, Methotrexate, or Tioguanine (formerly Thioguanine). Peptide antibiotics can include Bleomycin or Actinomycin. Platinum-based agents can include Carboplatin, Cisplatin, or Oxaliplatin. Retinoids can include Tretinoin, Alitretinoin, or Bexarotene. Vinca alkaloids and derivatives can include Vinblastine, Vincristine, Vindesine, or Vinorelbine.

Engineering of Treatment Resistant Circulating Tumor Cells to Produce Immune Inducing Exosomes Exosomes are small vesicles (30-100 nm) derived from the luminal membranes of late endosomes/multivesicular bodies (MVB) and are constitutively released via the fusion of MVBs with the cell membrane. Exosomes secreted by tumor cells have been implicated in all stages of tumor progression. Tumor exosomes are involved in the cell-cell communication, such as the horizontal transfer of information (i.e., mRNAs, microRNAs and proteins) between stem cells, endothelial cells, fibroblasts, bone marrow-derived cells (BMDCs), and tumor cells.

Immune-stimulating exosomes are those that express an immune stimulating protein, antibody, nucleic acid molecule, or compound on their surface, those that have an immune stimulating protein, antibody, nucleic acid molecule, or compound linked or associated with their surface, or those that have an immune stimulating protein, antibody, nucleic acid molecule, or compound in their lumen. Anti-cancer exosomes are those that express an anti-cancer protein, antibody, nucleic acid molecule, or compound on their surface, those that have an anti-cancer, antibody, nucleic acid molecule, or compound linked or associated with their surface, or those that have an anti-cancer protein, antibody, nucleic acid molecule, or compound in their lumen.

Exosome engineering can be divided into two approaches: parental cell-based or pre-isolation exosome engineering and direct or post-isolation exosome engineering. Parental cell-based engineering methods use genetic engineering for loading of therapeutic molecules into the lumen (loaded) or displaying them on the surface of exosomes (displayed). Post-isolation exosome engineering approaches use several chemical and mechanical methods including click chemistry, cloaking, bio-conjugation, sonication, extrusion, and electroporation.

The surface of exosomes can be modified to, for example, improve cell targeting or to display a therapeutic molecule like an antibody or binding portion thereof. Villata et al., Int. J. Mol. Sci (2020) 21:6048; Man et al., Nanomaterials. (2020) 10:1838; Chinnappan et al., Cancer Lett. (2020) 486:18-28. The surface of an exosome can be modified through modifying parental cells that will secrete exosomes or by directly modifying isolated exosomes. Antimisiaris et al., Pharmaceutics. (2018) 10:218. Modification of an exosome membrane can be done by genetic engineering of parental cells Zhang et al., Int. J. Nanomed. (2020) 15:6917-6934. Cells are genetically modified by, for example, the use of viral vectors to insert the coding sequence of the desired ligand. These cells then secrete exosomes with expressed peptides on their surface. Alternatively, methods can be used to modify the surface of exosomes after isolation from cells to achieve a more specific delivery to the target cells. Villata et al., Int. J. Mol. Sci. (2020) 21:6048. Surface modification of exosomes using covalent binding can be performed through crosslinking reactions, for example, click chemistry or azide-alkyne cycloaddition. A reaction between an alkyl and an azide chemical group can occur to form a stable triazole bond. See id. Additionally, the surface of exosomes can be altered through various non-covalent modification methods, such as receptor-ligand binding methods and multivalent electrostatic methods based on interactions between highly cationic species and negatively charged functional groups on the membrane Antimisiaris et al., Pharmaceutics. (2018) 10:218; Salunkhe et al., J. Control. Release. (2020) 326:599-614. Another method of exosome surface modification is hybridization, where exosomes combine with fusogenic liposomes due to the lipid nature of exosomes' membrane. Additionally, hydrophobic components can be incorporated directly onto the surface of exosomes. Man et al., Nanomaterials. (2020110:1838. Hydrophilic therapeutic cargoes, including hydrophilic drugs and macromolecules, such as siRNA, DNA, and proteins, can be incorporated into the core of exosomes. Zhang et al, Cel. Mol. Bioeng. (2020) 13:1-16; Hood et al., Nanomedicine. (2016) 11:1745-1756; Fu et al., NanoImpact. (2020) 20:100261; Donoso-Quezada at al, Crit. Rev. Biotechnol (2020) 40:804-820.

In some embodiments, exosomes can be engineered for surface display of therapeutic molecules using parental cell-based approaches. Using the parental cell-based approach of exosome engineering, the most common method for directing a protein to the surface of exosomes uses an exosomal signal peptide. For example, lysosome-associated membrane protein 2b ("Lamp2b", e.g., Lamp2b35) is an exosomal surface protein with an exosomal signal peptide. Fusion of a protein of interest to Lamp2b can be used for displaying the protein on the surface of exosomes as a targeting moiety, ligand, or receptor. Altogether, the signal peptide of Lamp2b can be used to display any fusion protein, therapeutic molecule, on the surface of exosomes.

In some embodiments, exosomes from CTCs can be engineered to express anti-cancer or immune-checkpoint inhibitory proteins such as anti-PD-L1, CTLA-4, LAG-3, TIM-3, TIGIT, VISTA, B7-H3, or the like on their surface or within their lumen. In some embodiments, exosomes from CTCs can be specific, meaning that they can be engineered to express particular cell surface proteins so that the engineered exosomes from CTCs target the correct tumor or tissue For example, nucleic acid molecules encoding anti-PD-L1 proteins such as antagonistic PD-L1 antibodies MED14736, LY3300054, or BMS-936559 can be fused to a nucleic acid molecule encoding Lamp2b (e.g., Lamp2b35) and the resulting complex utilized to engineer CTC-derived exosomes expressing anti-PD-L1 on the surface. In some embodiments, antibodies, siRNAs, or pharmacologic agents could be used to target one or more of the following genes: ABL1, ACVR1B, AKT1, AKT2, AKT3, ALK, ALOX12B, AMER1, (FAM123B), APC, AR, ARAF, ARFRP1, ARID1A, ASXL1, ATM, ATR, ATRX, AURKA, AURKB, AXIN1, AXL, BAP1, BARD1, BCL2, BCL2L1, BCL2L2, BCL6, BCOR, BCORL1, BRAF, BRCA1, BRCA2, BRD4, BRIP1, BTG1, BTG2, BTK, C11ORF30, (EMSY), CALR, CARD11, CASP8, CBFB, CBL, CCND1, CCND2, CCND3, CCNE1, CD22, CD274, (PD-L1), CD70, CD79A, CD79B, CDC73, CDH1, CDK12, CDK4, CDK6, CDK8, CDKN1A, CDKN16, CDKN2A, CDKN2B, CDKN2C, CEBPA, CHEK1, CHEK2, C1C, CREBBP, CRKL, CSF1R, CSF3R, CTCF, CTNNA1, CTNNB1, CUL3, CUL4A, CXCR4, CYP17A1, DAXX, DDR1, DDR2, DIS3, DNMT3A, DOT1L, EED, EGFR, EP300, EPHA3, EPHB1, EPHB4, ERBB2, ERBB3, ERBB4, ERCC4, ERG, ERRF11, ESR1, EZH2, FAM46C, FANCA, FANCC, FANCG, FANCL, FAS, FBXW7, FGF10, FGF12, FGF14, FGF19, FGF23, FGF3, FGF4, FGF6, FGFR1, FGFR2, FGFR3, FGFR4, FH, FLCN, FLT1, FLT3, FOXL2, FUBP1, GABRA6, GATA3, GATA4, GATA6, GID4, (C170RF39), GNA11, GNA13, GNAQ, GNAS, GRM3, GSK3B, H3F3A, HDAC1, HGF, HNF1A, HRAS, HSD3B1, ID3, IDH1, IDH2, IGF1R, IKBKE, IKZF1, INPP4B, IRF2, IRF4, IRS2, JAK1, JAK2, JAK3, JUN, KDM5A, KDM5C, KDM6A, KDR, KEAP1, KEL, KIT, KLHL6, KMT2A, (MLL), KMT2D, (MLL2), KRAS, LTK, LYN, MAF, MAP2K1, (MEK1), MAP2K2, (MEK2), MAP2K4, MAP3K1, MAP3K13, MAPK1, MCL1, MDM2, MDM4, MED12, MEF2B, MEN1, MERTK, MET, MITF, MKNK1, MLH1, MPL, MRE11A, MSH2, MSH3, MSH6, MST1R, MTAP, MTOR, MUTYH, MYC, MYCL, (MYCLI), MYCN, MYD88, NBN, NF1, NF2, NFE2L2, NFKB1A, NKX2-1, NOTCH1, NOTCH2, NOTCH3, NPM1, NRAS, NT5C2, NTRK1, NTRK2, NTRK3, P2RY8, PALB2, PARK2, PARP1, PARP2, PARP3, PAX5, PBRM1, PDCD1, (PD-1), PDCD1LG2, (PD-L2), PDGFRA, PDGFRB, PDK1, PIK3C2B, PIK3C2G, PIK3CA, PIK3CB, PIK3R1, P/MI, PMS2, POLD1, POLE, PPARG, PPP2R1A, PPP2R2A, PRDM1, PRKAR1A, PRKC1, PTCH1, PTEN, PTPN11, PTPRO, QKI, RAC1, RAD21, RAD51, RAD51B, RAD51C, RAD51D, RAD52, RAD54L, RAF1, RARA, RB1, RBM10, REL, RET, RICTOR, RNF43, ROS1, RPTOR, SDHA, SDHB, SDHC, SDHD, SETD2, SF3B1, SGK1, SMAD2, SMAD4, SMARCA4, SMARCB1, SMO, SNCA1P, SOCS1, SOX2, SOX9, SPEN, SPOP, SRC, STAG2, STAT3, STKI1, SUFU, SYK, TBX3, TEK, TET2, TGFBR2, TIPARP, TNFAIP3, TNFRSF14, TP53, TSC1, TSC2, TYRO3, U2AF1, VEGFA, VHL, WHSC1, (MMSET), WHSCIL1, WT1, XPO1, XRCC2, ZNF217, ZNF703, or combinations thereof. Antibodies, siRNAs and pharmaceutical agents that target these genes are known in the art.

In some embodiments, antibodies, siRNAs, or pharmacologic agents could be used to target one or more of the following kinases: Tyrosine-protein kinase ABL1, Activated CDC42 kinase 1, Activin receptor type-2A, Activin receptor type-2B, Uncharacterized aarF domain-containing protein kinase 4, Tribbles homolog 1, Serine/threonine-protein kinase BRSK2, Serine/threonine-protein kinase WNK2, RAC-alpha serine/threonine-protein kinase, RAC-beta serine/threonine-protein kinase, RAC-gamma serine/threonine-protein kinase, Calcium/calmodulin-dependent protein kinase type 1G, ALK tyrosine kinase receptor, Serine/threonine-protein kinase receptor R3, Activin receptor type-1, Bone morphogenetic protein receptor type-1A, Activin receptor type-1B, TGF-beta receptor type-1, Bone morphogenetic protein receptor type-1B, 5'-AMP-activated protein kinase catalytic subunit alpha-1, 5'-AMP-activated protein kinase catalytic subunit alpha-2, Atrial natriuretic peptide receptor 1, Atrial natriuretic peptide receptor 2, Serine/threonine-protein kinase A-Raf, Abelson tyrosine-protein kinase 2, Serine-protein kinase ATM, Serine/threonine-protein kinase ATR, Aurora kinase C, Tyrosine-protein kinase receptor UFO, Beta-adrenergic receptor kinase 1, [3-methyl-2-oxobutanoate dehydrogenase [lipoamide]] kinase, Mitogen-activated protein kinase 2, Tyrosine-protein kinase Blk, Serine/threonine-protein kinase B-raf, Protein-tyrosine kinase 6, Tyrosine-protein kinase BTK, Mitotic checkpoint serine/threonine-protein kinase BUB1 beta, Cyclin-dependent kinase 7, Calcium/calmodulin-dependent protein kinase type 1, Calcium/calmodulin-dependent protein kinase type 11 subunit alpha, Calcium/calmodulin-dependent protein kinase type I1 subunit beta, Calcium/calmodulin-dependent protein kinase (CaM kinase) I1 gamma, Calcium/calmodulin-dependent protein kinase type IV, CaM kinase-like vesicle-associated protein, Serine/threonine-protein kinase DCLK1, Peripheral plasma membrane protein CASK, Cyclin-dependent kinase 1, Cell division cycle 7-related protein kinase, Cyclin-dependent kinase 2, Cyclin-dependent kinase 3, Cyclin-dependent kinase 4, Cyclin-dependent kinase 5, Cyclin-dependent kinase 6, Cyclin-dependent kinase 8, cGMP-dependent protein kinase, cGMP-dependent protein kinase 2, Cyclin-dependent kinase 13, Serine/threonine-protein kinase Chk1, Serine/threonine-protein kinase Chk2, Casein kinase I isoform alpha, Casein kinase I isoform delta, Casein kinase I isoform epsilon, Casein kinase I isoform gamma-2, Casein kinase I isoform gamma-3, Casein kinase II subunit alpha, Casein kinase II subunit alpha', Dual specificity protein kinase CLK1, Dual specificity protein kinase CLK2, Dual specificity protein kinase CLK3, Mitogen-activated protein kinase 8, Macrophage colony-stimulating factor 1 receptor, Tyrosine-protein kinase CSK, MAP/microtubule affinity-regulating kinase 3, Retinal guanylyl cyclase 1, Retinal guanylyl cyclase 2, Death-associated protein kinase 1, Death-associated protein kinase 2, Mitogen-activated protein kinase 12, Myotonin-protein kinase, Serine/threonine-protein kinase MRCK gamma, DNA-dependent protein kinase catalytic subunit, Dual specificity tyrosine-phosphorylation-regulated kinase 1B, Dual specificity tyrosine-phosphorylation-regulated kinase 2, Dual specificity tyrosine-phosphorylation-regulated kinase 4, Eukaryotic elongation factor 2 kinase, Epidermal growth factor receptor, Interferon-induced, Serine/threonine-protein kinase MARK2, Ephrin type-A receptor 1, Ephrin type-A receptor 2, Ephrin type-A receptor 3, Ephrin type-A receptor 4, Ephrin type-A receptor 5, Ephrin type-A receptor 8, Ephrin type-B receptor 1, Ephrin type-B receptor 2, Ephrin type-B receptor 3, Ephrin type-B receptor 4, Ephrin type-B receptor 6, Mitogen-activated protein kinase 3, Mitogen-activated protein kinase 1, Mitogen-activated protein kinase 6, Mitogen-activated protein kinase 4, Focal adhesion kinase 1, Tyrosine-protein kinase Fer, Tyrosine-protein kinase Fes/Fps, Fibroblast growth factor receptor 1, Fibroblast growth factor receptor 2, Fibroblast growth factor receptor 3, Fibroblast growth factor receptor 4, Tyrosine-protein kinase Fgr, Receptor-type tyrosine-protein kinase FLT3, Vascular endothelial growth factor receptor 1, Vascular endothelial growth factor receptor 3, Serine/threonine-protein kinase mTOR, Tyrosine-protein kinase Fyn, Cyclin-G-associated kinase, G protein-coupled receptor kinase 4, G protein-coupled receptor kinase 5, G protein-coupled receptor kinase 6, Tribbles homolog 2, Glycogen synthase kinase-3 alpha, Glycogen synthase kinase-3 beta, Tyrosine-protein kinase HCK, Receptor tyrosine-protein kinase erbB-2, Receptor tyrosine-protein kinase erbB-3, Receptor tyrosine-protein kinase erbB-4, Homeodomain-interacting protein kinase 1, Mitogen-activated protein kinase 1, Heat-stable enterotoxin receptor, Insulin-like growth factor 1 receptor, Inhibitor of nuclear factor kappa-B kinase subunit alpha, Inhibitor of nuclear factor kappa-B kinase subunit beta, Integrin-linked protein kinase, Insulin receptor, Interleukin-1 receptor-associated kinase 1, Interleukin-1 receptor-associated kinase-like 2, Interleukin-1 receptor-associated kinase 3, Serine/threonine-protein kinase/endoribonuclease IRE1, Insulin receptor-related protein, Tyrosine-protein kinase ITK/TSK, Tyrosine-protein kinase JAK1, Tyrosine-protein kinase JAK2, Tyrosine-protein kinase JAK3, Mitogen-activated protein kinase 8, Mitogen-activated protein kinase 9, Mitogen-activated protein kinase 10, Mitogen-activated protein kinase 5, Inhibitor of nuclear factor kappa-B kinase subunit epsilon, NUAK family SNF1-like kinase 1, Microtubule-associated serine/threonine-protein kinase 3, Serine/threonine-protein kinase 36, Serine/threonine-protein kinase pim-3, Mast/stem cell growth factor receptor Kit, Cyclin-dependent kinase-like 2, Cyclin-dependent kinase-like 1, Kinase suppressor of Ras 1, Tyrosine-protein kinase Lck, LIM domain kinase 2, Serine/threonine-protein kinase STK11, Leukocyte tyrosine kinase receptor, Tyrosine-protein kinase Lyn, Serine/threonine-protein kinase MAK, MAP kinase-activated protein kinase 2, MAP kinase-activated protein kinase 3, MAP kinase-activated protein kinase 5, Serine/threonine-protein kinase MARK1, Microtubule-associated serine/threonine-protein kinase 2, Dual specificity mitogen-activated protein kinase 1, Dual specificity mitogen-activated protein kinase 2, Dual specificity mitogen-activated protein kinase 5, Dual specificity mitogen-activated protein kinase 6, Mitogen-activated protein kinase 1, Mitogen-activated protein kinase 2, Mitogen-activated protein kinase 3, Mitogen-activated protein kinase 4, Mitogen-activated protein kinase 5, Tyrosine-protein kinase Mer, Hepatocyte growth factor receptor, Anti-Muellerian hormone type-2 receptor, Dual specificity mitogen-activated protein kinase 7, Myosin light chain kinase, Mitogen-activated protein kinase 9, Mitogen-activated protein kinase 10, Dual specificity tyrosine-phosphorylation-regulated kinase 1A, MAP kinase-interacting serine/threonine-protein kinase 1, MAP kinase-interacting serine/threonine-protein kinase 2, Proto-oncogene serine/threonine-protein kinase mos, Dual specificity mitogen-activated protein kinase 3, Dual specificity mitogen-activated protein kinase 4, Serine/threonine-protein kinase MRCK beta, Ribosomal protein S6 kinase alpha-5, Ribosomal protein S6 kinase alpha-4, Serine/threonine-protein kinase 4, Serine/threonine-protein kinase 3, Serine/threonine-protein kinase 24, Muscle, Membrane-associated tyrosine- and threonine-specific cdc2-inhibitory kinase, Serine/threonine-protein kinase 38, Serine/threonine-protein kinase Nek1, Serine/threonine-protein kinase Nek2, Serine/threonine-protein kinase Nek3, Mitogen-activated protein kinase 14, Serine/threonine-protein kinase NLK, Serine/threonine-protein kinase Nek4, Interleukin-1 receptor-associated kinase 4, Phosphoinositide 3-kinase regulatory subunit 4, Rho-associated protein kinase 2, Mitogen-activated protein kinase 14, Ribosomal protein S6 kinase beta-1, Ribosomal protein S6 kinase beta-2, Serine/threonine-protein kinase PAK 1, Serine/threonine-protein kinase PAK 2, Serine/threonine-protein kinase PAK 3, Protein kinase C eta type, Cyclin-dependent kinase 16, Cyclin-dependent kinase 17, Cyclin-dependent kinase 18, Platelet-derived growth factor receptor alpha, Platelet-derived growth factor receptor beta, 3-phosphoinositide-dependent protein kinase 1, [Pyruvate dehydrogenase [lipoamide]] kinase isozyme 1, [Pyruvate dehydrogenase [lipoamide]] kinase isozyme 2, [Pyruvate dehydrogenase [lipoamide]] kinase isozyme 3, [Pyruvate dehydrogenase [lipoamide]] kinase isozyme 4, Eukaryotic translation initiation factor 2-alpha kinase 3, Cyclin-dependent kinase 14, Phosphorylase b kinase gamma catalytic chain, Phosphorylase b kinase gamma catalytic chain, Serine/threonine-protein kinase pim-1, Serine/threonine-protein kinase pim-2, Cyclin-dependent kinase 10, Cyclin-dependent kinase 9, Cyclin-dependent kinase 11B, Maternal embryonic leucine zipper kinase, Serine/threonine-protein kinase MRCK alpha, cAMP-dependent protein kinase catalytic subunit alpha, cAMP-dependent protein kinase catalytic subunit beta, cAMP-dependent protein kinase catalytic subunit gamma, Protein kinase C alpha type, Protein kinase C beta type, Protein kinase C delta type, Protein kinase C epsilon type, Protein kinase C gamma type, Protein kinase C iota type, Serine/threonine-protein kinase D1, Protein kinase C theta type, Protein kinase C zeta type, cAMP-dependent protein kinase catalytic subunit PRKX, Homeodomain-interacting protein kinase 3, Serine/threonine-protein kinase PLK1, Serine/threonine-protein kinase PLK3, Serine/threonine-protein kinase N1, Serine/threonine-protein kinase N2, Serine/threonine-protein kinase PRKY, Serine/threonine-protein kinase PRP4 homolog, Serine/threonine-protein kinase H1, RAF proto-oncogene serine/threonine-protein kinase, Proto-oncogene tyrosine-protein kinase receptor Ret, Rhodopsin kinase, Receptor-interacting serine/threonine-protein kinase 1, Receptor-interacting serine/threonine-protein kinase 2, Receptor-interacting serine/threonine-protein kinase 3, Rho-associated protein kinase 1, Macrophage-stimulating protein receptor, Tyrosine-protein kinase transmembrane receptor ROR1, Tyrosine-protein kinase transmembrane receptor ROR2, Proto-oncogene tyrosine-protein kinase ROS, Ribosomal protein S6 kinase alpha-2, Ribosomal protein S6 kinase alpha-3, Ribosomal protein S6 kinase alpha-1, Tyrosine-protein kinase RYK, Serine/threonine-protein kinase PLK4, Mitogen-activated protein kinase 11, Mitogen-activated protein kinase 12, Mitogen-activated protein kinase 13, Microtubule-associated serine/threonine-protein kinase 1, Serine/threonine-protein kinase Sgk1, STE20-like serine/threonine-protein kinase, Serine/threonine-protein kinase PLK2, Mitogen-activated protein kinase 11, Proto-oncogene tyrosine-protein kinase Src, SRSF protein kinase 1, SRSF protein kinase 2, Cyclin-dependent kinase-like 5, Serine/threonine-protein kinase TAO2, Tyrosine-protein kinase SYK, Mitogen-activated protein kinase 7, Bone morphogenetic protein receptor type-2, Tyrosine-protein kinase Tec, Angiopoietin-1 receptor, Dual specificity testis-specific protein kinase 1, TGF-beta receptor type-2, Tyrosine-protein kinase receptor Tie-1, Titin, Serine/threonine-protein kinase tousled-like 1, Serine/threonine-protein kinase tousled-like 2, Non-receptor tyrosine-protein kinase TNK1, Triple functional domain protein, High affinity nerve growth factor receptor, BDNF/NT-3 growth factors receptor, NT-3 growth factor receptor, Transformation/transcription domain-associated protein, Dual specificity protein kinase TTK, Tyrosine-protein kinase TXK, Non-receptor tyrosine-protein kinase TYK2, Tyrosine-protein kinase receptor TYRO3, Serine/threonine-protein kinase ULK1, Serine/threonine-protein kinase ULK2, Serine/threonine-protein kinase VRK1, Serine/threonine-protein kinase VRK2, Wee1-like protein kinase, Tyrosine-protein kinase Yes, Serine/threonine-protein kinase 25, Tyrosine-protein kinase ZAP-70, Mitogen-activated protein kinase 13, Epithelial discoidin domain-containing receptor 1, Uncharacterized aarF domain-containing protein kinase 1, Vascular endothelial growth factor receptor 2, Activin receptor type-1C, Aurora kinase B, Aurora kinase A, Mitogen-activated protein kinase 7, Mitotic checkpoint serine/threonine-protein kinase BUB1, Discoidin domain-containing receptor 2, Inactive tyrosine-protein kinase 7, LIM domain kinase 1, Serine/threonine-protein kinase LMTK1, Serine/threonine-protein kinase LMTK2, Serine/threonine-protein kinase LMTK3, Ephrin type-A receptor 7, Cytoplasmic tyrosine-protein kinase BMX, Megakaryocyte-associated tyrosine-protein kinase, Tyrosine-protein kinase FRK, Serine/threonine-protein kinase Nek6, Serine/threonine-protein kinase Nek7, AP2-associated protein kinase 1, Transient receptor potential cation channel subfamily M member 7, Protein-tyrosine kinase 2-beta, Tyrosine-protein kinase Srms, Serine/threonine-protein kinase 10, Mitogen-activated protein kinase 3, Serine/threonine-protein kinase OSR1, Serine/threonine-protein kinase PAK 6, Serine/threonine-protein kinase PAK 4, Serine/threonine-protein kinase MST4, STE20/SPS1-related proline-alanine-rich protein kinase, STE20-related kinase adapter protein alpha, STE20-related kinase adapter protein beta, Serine/threonine-protein kinase TAO3, Serine/threonine-protein kinase TAO1, Mitogen-activated protein kinase 4, TRAF2 and NCK-interacting protein kinase, Misshapen-like kinase 1, Nik-related protein kinase, Serine/threonine-protein kinase LATS1, Serine/threonine-protein kinase LATS2, Cyclin-dependent kinase 19, Serine/threonine-protein kinase NIM1, Serine/threonine-protein kinase ULK3, Serine/threonine-protein kinase PDIK1L, Tau-tubulin kinase 2, N-terminal kinase-like protein, Serine/threonine-protein kinase greatwall, Serine/threonine-protein kinase PINK1, Serine/threonine-protein kinase ULK4, Mixed lineage kinase domain-like protein, Serine/threonine-protein kinase DCLK3, Protein kinase domain-containing protein, Cyclin-dependent kinase 15, Serine/threonine-protein kinase 33, TP53-regulating kinase, Mitogen-activated protein kinase 15, Cyclin-dependent kinase-like 4, Protein-associating with the carboxyl-terminal domain of ezrin, Serine/threonine-protein kinase 32C, Serine/threonine-protein kinase Nek9, Testis-specific serine/threonine-protein kinase 3, NUAK family SNF1-like kinase 2, Ribosomal protein S6 kinase-like 1, Testis-specific serine/threonine-protein kinase 2, SCY1-like protein 2, Serine/threonine-protein kinase Nek8, Beta-adrenergic receptor kinase 2, Nuclear receptor-binding protein, Serine/threonine-protein kinase D2, Serine/threonine-protein kinase 32B, Calcium/calmodulin-dependent protein kinase 2, Cyclin-dependent kinase 20, Dual specificity protein kinase CLK4, Cyclin-dependent kinase 12, Serinelthreonine-protein kinase 17A, Serine/threonine-protein kinase 17B, Dual specificity tyrosine-phosphorylation-regulated kinase 3, Serine/threonine-protein kinase D3, Eukaryotic translation initiation factor 2-alpha kinase 4, Uncharacterized serine/threonine-protein kinase SgK494, Serine/threonine-protein kinase 40, Serine/threonine-protein kinase 35, Serine/threonine-protein kinase TNN13K, Homeodomain-interacting protein kinase 2, Eukaryotic translation initiation factor 2-alpha kinase 1, Serine/threonine-protein kinase ICK, Serine/threonine-protein kinase/endoribonuclease IRE2, PAS domain-containing serine/threonine-protein kinase, Serine/threonine-protein kinase 38-like, Serine/threonine-protein kinase SIK3, Hormonally up-regulated neu tumor-associated kinase, Mitogen-activated protein kinase 6, Mitogen-activated protein kinase MLT, MAPK/MAK/MRK overlapping kinase, Serine/threonine-protein kinase 16, SRSF protein kinase 3, Serine/threonine-protein kinase WNK1, Cyclin-dependent kinase-like 3, Serine/threonine-protein kinase PAK 7, Serine/threonine-protein kinase N3, Serine/threonine-protein kinase SIK2, MAP/microtubule affinity-regulating kinase 4, Dual serine/threonine and tyrosine protein kinase, Ribosomal protein S6 kinase delta-1, Ribosomal protein S6 kinase alpha-6, Nuclear receptor-binding protein 2, Protein kinase-like protein SgK071, Serine/threonine-protein kinase Sgk2, Testis-specific serine/threonine-protein kinase 6, Serine/threonine-protein kinase Sgk3, Tau-tubulin kinase 1, Serine/threonine-protein kinase DCLK2, PX domain-containing protein kinase-like protein, Lymphokine-activated killer T-cell-originated protein kinase, Tyrosine-protein kinase STYK1, Serine/threonine-protein kinase TBK1, Dual-specificity testis-specific protein kinase 2, HCG2039851, Testis-specific serine/threonine-protein kinase 4, Inactive serine/threonine-protein kinase VRK3, Myosin light chain kinase 3, Striated muscle preferentially expressed protein kinase, Casein kinase I isoform alpha-like, Receptor-interacting serine/threonine-protein kinase 4, Serine/threonine-protein kinase Nek5, Calcium/calmodulin-dependent protein kinase type 1D, Mitogen-activated protein kinase 19, Serine/threonine-protein kinase Nek11, G protein-coupled receptor kinase 7, Serine/threonine-protein kinase SBK2, Homeodomain-interacting protein kinase 4, Myosin-IIIb, Serine/threonine-protein kinase WNK4, Putative uncharacterized serine/threonine-protein kinase SgK110, Serine/threonine-protein kinase BRSK1, Obscurin, Serine/threonine-protein kinase H2, Serine/threonine-protein kinase SIK1, Kinase suppressor of Ras 2, Serine/threonine-protein kinase R103, Chaperone activity of bc1 complex-like, Serine/threonine-protein kinase RIO1, Serine/threonine-protein kinase 32A, SNF-related serine/threonine-protein kinase, Ephrin type-A receptor 10, Protein kinase-like protein SgK196, Myosin-IIIa, Serine/threonine-protein kinase WNK3, Tyrosine-protein kinase SgK223, Serine/threonine-protein kinase Nek10, Ephrin type-A receptor 6, Casein kinase I isoform gamma-1, Pseudopodium-enriched atypical kinase 1, Serine/threonine-protein kinase SBK1, Serine/threonine-protein kinase 31, Ankyrin repeat and protein kinase domain-containing protein 1, Serine/threonine-protein kinase Kist, Calcium/calmodulin-dependent protein kinase type 1B, TBC domain-containing protein kinase-like protein, Serine/threonine-protein kinase SMG1, Myosin light chain kinase 2, Mitogen-activated protein kinase 15, Leucine-rich repeat serine/threonine-protein kinase 2, Mitogen-activated protein kinase MLK4, Serine/threonine-protein kinase haspin, Tribbles homolog 3, Citron Rho-interacting kinase, Calcium/calmodulin-dependent protein kinase 1, Leucine-rich repeat serine/threonine-protein kinase 1, Inactive serine/threonine-protein kinase TEX14, Microtubule-associated serine/threonine-protein kinase 4, Calcium/calmodulin-dependent protein kinase type II subunit delta, BMP-2-inducible protein kinase, Testis-specific serine/threonine-protein kinase 1, Inactive serine/threonine-protein kinase TEX14, Myosin light chain kinase family member 4, Uncharacterized aarF domain-containing protein kinase 2, Death-associated protein kinase 3, Wee1-like protein kinase 2, 2-5A-dependent ribonuclease, Transient receptor potential cation channel subfamily M member 6, Serine/threonine-protein kinase RIO2, Alpha-protein kinase 2, Alpha-protein kinase 1, Bromodomain-containing protein 2, Bromodomain-containing protein 3, BRD4 protein, Bromodomain testis-specific protein, Alpha-protein kinase 3, Uncharacterized aarF domain-containing protein kinase 5, Transcription intermediary factor 1-alpha, Transcription intermediary factor 1-beta, E3 ubiquitin-protein ligase TRIM33, Tyrosine-protein kinase JAK1, Tyrosine-protein kinase JAK2, Tyrosine-protein kinase JAK3, Ribosomal protein S6 kinase alpha-5, Ribosomal protein S6 kinase alpha-4, Ribosomal protein S6 kinase alpha-2, Ribosomal protein S6 kinase alpha-3, Ribosomal protein S6 kinase alpha-1, Non-receptor tyrosine-protein kinase TYK2, Eukaryotic translation initiation factor 2-alpha kinase 4, Ribosomal protein S6 kinase alpha-6, Striated muscle preferentially expressed protein kinase, Obscurin, PAB-dependent poly(A)-specific ribonuclease subunit 3, Fas-activated serine/threonine kinase, Serine/threonine-protein kinase 19, Transcription initiation factor TFIID subunit 1, Transcription initiation factor TFIID subunit 1-like, Breakpoint cluster region protein, Active breakpoint cluster region-related protein, Tripartite motif-containing protein 66, nan, Collagen type IV alpha-3-binding protein, Biliverdin reductase A, Bromodomain adjacent to zinc finger domain protein 1A, Tyrosine-protein kinase BAZ1B, or combinations thereof. Antibodies, siRNA's and pharmaceutical agents that target these kinases are known in the art.

Additionally, CTCs engineered to comprise exosomes expressing immune-checkpoint inhibitory proteins such as anti-PD-L1 on their surface can be administered back into the patient to home back into the tumor sites and release exosomes with checkpoint inhibitory proteins. Those proteins will attach to PD-L1 receptors and block the ability of the tumor cells to inhibit immune response of killer T-cells.

Other commonly used molecules for exosomal surface display of fusion proteins include tetraspanins (CD63, CD9, CD81), glycosylphosphatidylinositol (GPI), platelet-derived growth factor receptors (PDGFRs), and lactadherin (C1C2 domain). In a very similar method to Lamp2b fusion proteins, the NH2-terminal of CD63 can be fused to a protein of interest for the same purpose. Other non-cellular and exosomal proteins such as vesicular stomatitis virus glycoprotein (VSVG) have also been used for surface display of proteins on exosomes.

In some embodiments, exosomes can be engineered for loading proteins or anti-cancer agents into the lumen of exosomes using parental cell-based approaches. These methods recruit the molecule sorting modules (MSMs) for sorting of proteins and RNAs into the lumen. These modules can bind to the protein or RNA of interest and direct them to exosomes. However, different MSMs or other modules can be used in different methods. In one method, an engineered ubiquitin tag (the last two glycine residues in the C-terminal are removed) has been developed. Removal of the two glycine residues results in enhanced ubiquitinated protein half-life. Fusion of this ub-tag to the proteins of interest, such as, for example, Ag85B and ESAT6 (*Mycobacterium tuberculosis* proteins) or enhanced green fluorescent protein (EGFP) and nHer2 (tumor antigens), leads to the loading of the proteins into the lumen of exosomes in human embryonic kidney (HEK293) cells.

In another method, a short tag (WW tag) with the ability to bind specifically to the L-domain motif of Ndfip1 (which activates HECT domain-containing E3 ubiquitin-protein ligases) can be used. The WW tag method is another system that uses ubiquitination for the loading of proteins into exosomes. For example, fusion of Cre recombinase (as a protein of interest) to the WW tag and simultaneous expression with Ndfip1 leads to recognition of the WW tag by Ndfip1 and activation of E3 ubiquitin ligases and ubiquitination of Cre. Subsequently, the ubiquitinated Cre-WW can be loaded into the exosomes. Ndfip1 protein induces the molecular switch for ubiquitination and helps with the exosomal packaging of the Cre-WW fusion protein.

In some embodiments, exosomes can be engineered for loading of RNAs into exosomes using parental cell-based engineering (e.g., Jafari, Davod, et al., *BioDrugs* 34.5, pgs. 567-586, 2020). In some embodiments, a parental cell-based strategy for loading mRNAs (e.g. EXOtic (Exosomal Transfer Into Cells)) can be used.

In some embodiments, treatment resistant CTCs can be engineered via transfection with viral vectors, transformation with plasmid vectors, lysosome incubation methods (e.g., use of lysosome-associated membrane protein 2b), or other suitable methods to produce immune-stimulating exosomes such as cytokines or immunotherapy targets.

There are a number of ways in which expression vectors can be introduced into cells. In some embodiments, an expression vector comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells.

One set of methods for in vivo delivery involves the use of an adenovirus, or adeno-associated virus expression vector. Adenovirus expression vectors include those constructs containing adenovirus sequences sufficient to (a) support packaging of the construct and (b) to express an polynucleotide that has been cloned therein.

If desired, polynucleotides can be cloned into an expression vector comprising expression control elements, including for example, origins of replication, promoters, enhancers, or other regulatory elements that drive expression of the polynucleotides in CTCs. An expression vector can be, for example, a plasmid, such as pBR322, pUC, or ColE1, or an adenovirus (AdV) vector, such as an adenovirus Type 2 vector or Type 5 vector, an adeno-associated virus (AAV) vector, a retrovirus vector, a lentivirus (LV) vector, a herpes simplex virus (HSV) vector, or a baculovirus vector. A retroviral vector can also be, e.g., a gammaretroviral vector such as, for example, Murine Leukemia Virus (MLV), Spleen-Focus Forming Virus (SFFV), and Myeloproliferative Sarcoma Virus (MPSV), and vectors derived therefrom. A lentivirus can be, for example, human immunodeficiency virus (HIV), simian immunodeficiency virus (SIV), or feline immunodeficiency virus (FIV). Optionally, other vectors can be used, including but not limited to Sindbis virus, simian virus 40, alphavirus vectors, poxvirus vectors, bovine papilloma virus vectors, and cytomegalovirus and retroviral vectors, such as murine sarcoma virus, mouse mammary tumor virus, Moloney murine leukemia virus, and Rous sarcoma virus. Still other vectors can be used, including but not limited to paramyxovirus (PIV) vector, such as bovine parainfluenza virus (BPIV) vector (e.g., a BPIV-1, BPIV-2, or BPV-3 vector) or human PIV vector, a metapneumovirus (MPV) vector, a Sendia virus vector, or a measles virus vector. Mini-chromosomes such as MC and MC1, bacteriophages, phagemids (e.g., pBluescript IIKs), yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

To confirm the presence of recombinant polynucleotides or recombinant genes in transgenic cells, a polymerase chain reaction (PCR) amplification or Southern blot analysis can be performed using methods known to those skilled in the art. Expression products of the recombinant polynucleotides or recombinant genes can be detected in any of a variety of ways, and include for example, western blot and enzyme assay.

Other expression constructs that can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific.

Receptor-mediated gene targeting vehicles generally comprise of two components: a cell receptor-specific ligand and a DNA-binding agent. Several ligands have been used for receptor-mediated gene transfer. The most extensively characterized ligands are asialoorosomucoid (ASOR) and transferrin. For example, a synthetic neoglycoprotein, which recognizes the same receptor as ASOR, has been used as a gene delivery vehicle and epidermal growth factor (EGF) has also been used to deliver genes to squamous carcinoma cells.

Exosomes derived from cultured cells can be used for delivery of siRNA in vitro and in vivo. Targeted exosomes can be made through transfection of an expression vector comprising an exosomal protein fused with a peptide ligand. The exosomes can be purified from transfected cell supernatant and siRNA loaded into exosomes. See, e.g., El-Andaloussi et al., Nature Protocols, 7:2112-2126 (2012). In an example, exosomes derived from normal fibroblast-like mesenchymal cells were engineered to carry short interfering RNA or short hairpin RNA specific to oncogenic $Kras^{G12D}$, a common mutation in pancreatic cancer. See Kamerkar et al, Nature 546: 498-503 (2017). In an example, cells can be cultured and co-transfected with plasmids encoding exosomal membrane protein such as Lamp2b, optionally in fusion with a tumor-penetrating internalizing protein such as iRGD ((CRGDKGPDC SEQ ID NO:1) and siRNA using, for example lipofectamine. The cell culture medium can be collected after transfection, and the exosomes harvested from the cultural medium with, for example, Exosome Isolation Reagent (invitrogen) The resulting pellet can be resuspended in PBS.

In some embodiments, exosomes can be engineered using a post-isolation approach (e.g., Jafari, Davod, et al., BioDrugs 34.5, pgs. 567-586, 2020). Drugs and therapeutic agents can be encapsulated into purified exosomes by post-isolation modification methods directly after their isolation from cells, which can provide good efficiency. Small nucleic acid molecules (e.g., miRNAs and short interfering RNAs (siRNAs)) and therapeutic molecules such as anti-cancer agents can be encapsulated in exosomes by direct exosome engineering (Xu, Zhijie, et al., *Molecular Cancer,* 19.1, pgs. 1-16, 2020). This type of exosome engineering can be technically less complex compared with the parental cell-based methods. Post-isolation methods include, for example, active and passive incorporation. Jafari et al. BioDrugs. (2020) 34:567-586; Antimisiaris et al., Pharmaceutics. (2018) 10:218; Man et al., Nanomaterials. (2020) 10:1838. Passive incorporation methods are simple and can preserve the morphology of exosomes with a low loading efficiency. Methods include co-incubation of exosomes and therapeutic agents, which diffuse into the interior of exosomes through the membrane along the concentration gradient. Villata et al. int. J. Mol. Sci. (2020) 21:6048. Several types of active incorporation methods exist. Villata et al., Int. J Mol. Sci. (2020) 21:6048. These methods can temporarily disrupt the membrane, allowing the cargo to easily pass into the interior of the exosomes. After the diffusion of the cargo, the membrane integrity of the exosomes can be restored. Akuma et al. Front. Sustain, Food Syst. (2019) 3:23. Electroporation can be used to temporarily form pores in the phospholipid bilayer of exosomes with an electric field in a conductive solution, allowing the entry of cargo into exosomes. Examples include the incorporation of fluorescent Atto655-conjugated nonspecific siRNA into exosomes derived from human embryonic kidney cells by electroporation with 10-20% efficiency and encapsulation of galectin-9 siRNA into exosomes derived from bone marrow mesenchynmal stem cells by electroporation, Faruqu et al. J. Vis. Exp. (2018) 142: e58814.

Extrusion, where a mixture of exosomes and cargo is extruded through a membrane with a pore size between, for example, 100 and 400 nm using a lipid extruder can also be used. The cargo enters inside the exosomes through a disrupted membrane, See e.g., Antimisiaris et al., Pharmaceutics. (2018) 10:218. A freeze-thaw method can also be used to load exosomes. For example, several cycles of freezing the exosome-cargo mixture at −80° C. or in liquid nitrogen and re-thawing to room temperature are repeated to ensure the successful incorporation of drugs or nucleic acid molecules. Another method is chemical transfection where exosomes and cargo are incubated with a surfactant such as saponin, causing the formation of pores in the membrane and thus the penetration of drugs or nucleic acid molecules. Villata et al., Int. J. Mot. Sci. (2020) 21:6048.

Hydrophilic compounds are not able to pass naturally through the lipid bilayer; therefore, many methods have been developed to incorporate various compounds into exosomes. These methods can, for example, create pores through which hydrophilic compounds can enter exosomes. Das et al. Mol. Pharm. (2019) 16:24-40. Methods such as co-incubation, saponin-assisted loading, the freeze-thaw method, sonication, and extrusion can effectively incorporate proteins, polypeptides, and nucleic acid molecules without altering the structure of the exosomes significantly. Tran et al. Int. J. Pharm. (2019) 566:697-707.

In post-isolation approaches, manipulation methods of electroporation, extrusion, sonication, incubation, freeze-thaw, bio-conjugation, click chemistry, and cloaking can be used for direct engineering of exosomes after isolation from cells.

Clustered Regularly Interspersed Short Palindromic Repeats (CRISPR)/CRISPR-associated (Cas) systems or components of such systems can be used to modify a genome within a cell. CRISPR/Cas systems include transcripts and other elements involved in the expression of, or directing the activity of, Cas genes. A CRISPR/Cas system can be a type 1, a type 11, or a type Ill system. CRISPR complexes (comprising a guide RNA (gRNA) complexed with a Cas protein) can be used for site-directed cleavage of nucleic acids.

CRISPR technologies can be used to genetically engineer CTC cells. Such systems can employ a Cas9 nuclease (or other suitable nuclease), which in some instances, is codon-optimized for the desired cell type in which it is to be expressed. The system further employs RNA, which is often referred to as a guide RNA or gRNA. In some embodiments, a short DNA fragment containing a target sequence is inserted into a guide RNA expression plasmid. The gRNA expression plasmid comprises the target sequence as well as a suitable promoter that is active in the cell and necessary elements for proper processing in eukaryotic cells. CRISPR systems can rely on custom, complementary oligos that are annealed to form a double stranded DNA and then cloned into the gRNA expression plasmid. The gRNA expression cassette and the Cas9 expression cassette can then be introduced into the cell. See, for example, Mali et al. (2013) Science 2013 Feb. 15; 339 (6121):823-6; Jinek et al. Science 2012 Aug. 17; 337(6096):816-21; Hwang et al. Nat Biotechnol 2013 March; 31(3):227-9; Jiang et al. Nat Biotechnol 2013 March; 31(3):233-9; Cong et al. Science 2013 Feb. 15; 339(6121):819-23, each of which is herein incorporated by reference.

Localized Response

In some embodiments, a cancer patient is treated by inducing a localized response using the isolated treatment resistant CTCs engineered to produce immune-stimulating exosomes. See, e.g., FIG. 1 "Path 1." The isolated treatment resistant CTCs engineered to produce immune-stimulating exosomes can be directly injected into the tumor or near the primary tumor in the patient to self-home to the primary tumor and metastatic lesions. Upon release, CTC exomes can, for example, present antigens that stimulate T cells and trigger T cell-dependent anti-tumor responses or otherwise stimulate the immune response of the patient in the area of the primary tumor and/or metastatic lesions.

Isolation of Exosomes and Induction of Systemic Response

In an embodiment, exosomes can be isolated from treatment resistant circulating tumor cells, which are isolated from a population of circulating tumor cells as described above. Exosomes can have immune modulating roles in cancers. Many different types of cells secrete exosomes; in the case of cancerous cells, exosomes typically promote tumor growth and metastasis while suppressing immune function. Exosomes containing large amounts of tumor antigens on MHC 1 and heat shock proteins (HSP) can be involved in antigen presentation and stimulation of anti-tumor immune responses in vitro and in vivo.

Exosomes can be isolated using any suitable method including, for example, ultracentrifugation, pellet-down by centrifugation, fractionation by particle size, immunoprecipitation methods and the like.

In ultracentrifugation methods, exosomes are precipitated and isolated by ultracentrifugation of the sample (e.g., centrifugation at 100000×g for 70 minutes for 2-3 minutes). In fractionation methods, a density gradient solution such as sucrose is used to fractionate on the basis of size or density (density gradient fractionation method).

Another method for isolation of exosomes is polymer precipitation, which is a simple method based on changing the solubility of the exosomes. See Bunggulawa et al. J. Nanobiotechnol. (2018) 16:81. Antimisiaris et al., Pharmaceutics. (2018) 10:218. Pellet-down by centrifugation comprises adding a reagent (polymer) to a sample and concentrating it by precipitating exosomes using a centrifuge.

Fractionation by particle size is a technique of putting samples through a plurality of filters (usually 2 to 3) to capture exosomes. In one example, where two filters are used, large particles can be removed using a first filter of about 200 nm pore size and exosomes can be captured using a second about 20 nm pore size filter.

Immunoprecipitation can recover exosomes comprising a specific protein, using magnetic beads on which an antibody against the protein is immobilized. In immunoprecipitation, it is possible to capture exosomes in which specific exosomal antigens (e.g., CD9, CD63, CD81, etc.) are present on the surface, and by using different antibodies, various exosomal membrane surface antigens are targeted.

Once the exosomes are isolated, they can be co-incubated ex vivo with dendritic cells to form a population of exosome-loaded dendritic cells. Dendritic cells represent the sentinels of the immune system and play an important role in linking the innate and adaptive immune responses. They are powerful antigen presenting cells (APCs), given their ability to stimulate unprimed (naïve) helper and cytotoxic T cells and perform antigen cross-presentation. The dendritic cells can take up the exosomes in culture. Briefly, in an example, monocytes can be purified from total PBMCs using anti-CD14 antibody-conjugated magnetic beads (Miltenyi Biotec, Auburn, CA, USA) and cultured at various densities in a multi-well plate containing serum-free X-VIVO15 medium (Lonza). After about 1, 2, 3, 4, 5, 6, 7, 8, 9, 10, or more days, the dendritic cells can be harvested and seeded in a multi-well plate for co-culture with engineered exosomes at different ratios. Co-incubation can be tested using any suitable method such as, for example, flow cytometry.

The exosome-loaded dendritic cells can then be administered by, for example infusion to the patient to elicit a systemic immune response. See, e.g., FIG. 1, "Path 2." A systemic immune response is an immune response occurring outside of the localized tumor microenvironment. The tumor immunology field has focused on local immune responses in the localized tumor microenvironment, even though immunity is coordinated across tissues. For example, myeloid cells are replenished from hematopoietic precursors in the bone marrow, critical T cell priming events typically occur in lymphoid tissues, and virtually every subset of immune cell has been implicated in cancer biology. A localized anti-tumor immune response requires continuous communication with the periphery. Exosome-loaded dendritic cells can be used to engage a systemic immune response occurring outside of the localized tumor microenvironment.

Treatment of Cancer Patients

Treatment resistant CTCs engineered to produce immune-stimulating exosomes can be administered (e.g., by infusion or injection) to cancer patients and/or exosome-loaded dendritic cells can be administered (e.g., by infusion or injection) to cancer patients. In some embodiments, treatment resistant CTCs engineered to produce immune-stimulating exosomes or exosome-loaded dendritic cells can be injected into cancer patients, such as injected at, into, or near a tumor site. In some embodiments, a patient can have kidney cancer such as clear cell kidney cancer, urothelial carcinoma, sarcoma of the kidney, Wilms tumor, or kidney lymphoma. In an embodiment a patient has bladder cancer, breast cancer, colon cancer, rectal cancer, endometrial cancer, leukemia, liver cancer, lung cancer (e.g., non-small cell lung cancer or small cell lung cancer), melanoma, non-Hodgkin lymphoma, pancreatic cancer, prostate cancer, thyroid cancer, parathyroid cancer, neuroblastoma, lymphoma, adrenocortical cancer, sarcoma, bile duct cancer, brain cancer, bone cancer, gastrointestinal cancer, cardiac cancer, cervical cancer, chronic myeloproliferative neoplasm, esophageal cancer, head and neck cancer, retinoblastoma, gall bladder cancer, testicular cancer, ovarian cancer, laryngeal cancer, or any other cancer.

Treatment resistant CTCs engineered to produce immune-stimulating exosomes can be injected into a cancer patient to self-home to the primary tumor and metastatic lesions (e.g., Garcia-Castro, Javier, et al., *Cancer gene therapy* 12.4, pgs. 341-349, 2005). Tumor "self-homing" describes the recruitment of circulating tumor cells (CTCs) back to a previously excised primary tumor location, contributing to tumor recurrence, as well as their migration to established metastatic lesions. In some embodiments, following injection of altered CTCs, CTC exosomes can present antigens that stimulate T cells and trigger T cell-dependent anti-tumor responses. In some embodiments, exosome-loaded dendritic cells can be injected into a cancer patient.

Exosome-loaded dendritic cells can also be infused into a cancer patient to elicit a systemic immune response.

Infusion can be facilitated by the use of a pump. In some embodiments, infusion can be continuous. In some embodiments, a small needle can be placed into the vein, usually in the arm or hand, of a patient. The blood then moves from a bag, through a tube, and into the patient's vein through the needle. In some embodiments, infusion of cells can take about 20, 30, 40, 50, 60, or more minutes. In some embodiments infusion of cells can take about 1, 2, 3, 4, 5, 6, 7, or more hours.

Sequentially, Simultaneously, or Stand-Alone

In some embodiments, a method of treating a cancer patient can comprise one or more of the steps of path 1 (FIG. 1), which can induce a localized immune response. In some embodiments, path 1 can comprise the steps of (a) extracting circulating tumor cells from a cancer patient to produce a population of isolated circulating tumor cells; (b) isolating a population of treatment resistant circulating tumor cells from the population of isolated circulating tumor cells; (c) genetically engineering the treatment resistant circulating tumor cells to generate immune stimulating or anti-cancer exosomes thereby producing a population of genetically engineered treatment resistant circulating tumor cells; and (d) administering the genetically engineered treatment resistant circulating tumor cells into the cancer patient.

In some embodiments, a method of treating a cancer patient can comprise the steps (a)-(d) of path 1 listed above and, sequentially or simultaneously, the steps of path 2 (FIG. 1), which can induce a systemic immune response. In some embodiments, path 2 can comprise the steps of (a) harvesting exosomes from the population of treatment resistant circulating tumor cells to produce a population of isolated treatment resistant circulating tumor cell exosomes; (b) incubating the population of isolated treatment resistant circulating tumor cell exosomes with dendritic cells to form a population of exosome-loaded dendritic cells; and (c) administering the population of exosome-loaded dendritic cells into the cancer patient. In some embodiments, administering can comprise infusing the population of exosome-loaded dendritic cells into the cancer patient. In some embodiments, administering can comprise injecting the population of exosome-loaded dendritic cells into the cancer patient.

In some embodiments, a method of treating a cancer a patient can comprise path 2 alone or path 1 alone. In some embodiments, the injection step of path 1, step (d), can be administered alone. In some embodiments, the administration (e.g., infusion or injection) step of path 2, step (e), can be administered alone. In some embodiments, the injection step of path 1, step (d), can be administered simultaneously with the administration (e.g., infusion or injection) step of path 2, step (c). In some embodiments, the injection step of path 1, step (d), can be administered at a different time from the administration (e.g., infusion or injection) step of path 2, step (c). Any two administrations (where one administration follows path 1 and one administration follows path 2, where both administrations follow step 1, or both administrations follow path 2) can be separated by about 5, 10, 15, 20, 30, 40, 50, 60, or more minutes. The two administration steps can be separated by about 1, 2, 3, 4, 5, 6, 7, 8, 9, 10, 11, 12, 13, 14, 15, 16, 17, 18, 19, 20, 21, 22, 23, 24, or more hours. Any two administration steps can be separated by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or more days. Any two administration steps can be separated by about 1, 2, 3, 4, 5, 6, 7, 8, 9, 10, 11, 12, 13, 14, 15, 16, 17, 18, 19, 20, 21, 22, 23, 24, or more moths. In some embodiments, an injection step of path 1, step (d) can be administered prior to the administration (e.g., infusion or injection) step of path 2, step (c). In some embodiments, an administration (e.g., infusion or injection) step of path 2, step (c), can be administered prior to the injection step of path 1, step (d). In some embodiments, any two administration steps follow path 2 can be injections, infusions, or combinations thereof.

In some embodiments, treatment resistant CTCs can be derived from a cancer patient and administered to the same cancer patient. In some embodiments, treatment resistant CTCs can be derived from a cancer patient and administered to other cancer patients. In some embodiments, engineered immune stimulating or anti-cancer exosomes can be derived from a cancer patient and administered to the same cancer patient. In some embodiments, engineered immune stimulating or anti-cancer exosomes can be derived from a cancer patient and administered to other cancer patients. In some embodiments, treatment resistant CTCs can be derived from a cancer patient to be treated, while the engineered immune stimulating or anti-cancer exosomes can be derived from other cancer patients. In some embodiments, the immune stimulating or anti-cancer exosomes can be derived from the cancer patient to be treated while the treatment resistant CTCs can be derived from other cancer patients.

In some embodiments, path 1 can be repeated 1, 2, 3, 4, 5, 6, 7, 8, 9, 10, or more times. In some embodiments, path 2 can be repeated 1, 2, 3, 4, 5, 6, 7, 8, 9, 10, or more times. In some embodiments, path 1 and path 2 can be administered sequentially 1, 2, 3, 4, 5, 6, 7, 8, 9, 10, or more times. In some embodiments path 1 and path 2 can be administered simultaneously 1, 2, 3, 4, 5, 6, 7, 8, 9, 10, or more times.

As used herein, the terms "treat," "treatment," "therapy," "therapeutic," and the like refer to obtaining a desired pharmacologic and/or physiologic effect, including, but not limited to, alleviating, delaying or slowing the progression, reducing the effects or symptoms, preventing onset, inhibiting, ameliorating the onset of a disease or disorder, obtaining a beneficial or desired result with respect to a disease, disorder, or medical condition, such as a therapeutic benefit and/or a prophylactic benefit. "Treatment," as used herein, covers any treatment of a disease in a mammal, particularly in a human, and includes: (a) preventing the disease from occurring in a subject that can be predisposed to the disease or at risk of acquiring the disease but has not yet been diagnosed as having it; (b) inhibiting the disease, i.e., arresting its development; and (c) relieving the disease, i.e., causing regression of the disease. A therapeutic benefit includes eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In some cases, for prophylactic benefit, compounds or compositions are administered to a subject at risk of developing a particular disease, or to a subject reporting one or more of the physiological symptoms of a disease, even though a diagnosis of the disease may not have been made. The methods of the present disclosure can be used with any mammal or other animal. In some cases, the treatment can result in a decrease or cessation of symptoms. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the term "subject" or refers to any individual or patient on which the methods disclosed herein are performed. The term "subject" can be used interchangeably with the term "individual" or "patient." The subject can be a human, although the subject may be an animal, as will be appreciated. Thus, other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Compositions and methods are more particularly described below and the Examples set forth herein are intended as illustrative only, as numerous modifications and variations therein will be apparent to those skilled in the art. The terms used in the specification generally have their ordinary meanings in the art, within the context of the compositions and methods described herein, and in the specific context where each term is used. Some terms have been more specifically defined herein to provide additional guidance to the practitioner regarding the description of the compositions and methods.

As used herein, the term "and/or" includes any and all combinations of one or more of the associated listed items. As used in the description herein and throughout the claims that follow, the meaning of "a", "an", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105).

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising," "consisting essentially of," and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods.

In addition, where features or aspects of the compositions and methods are described in terms of Markush groups or other grouping of alternatives, those skilled in the art will recognize that the compositions and methods are also thereby described in terms of any individual member or subgroup of members of the Markush group or other group.

I claim:

1. A method of treating a cancer patient comprising:
(a) extracting circulating tumor cells from the cancer patient to produce a population of isolated circulating tumor cells;
(b) isolating a population of treatment resistant circulating tumor cells from the population of isolated circulating tumor cells;
(c) genetically engineering the treatment resistant circulating tumor cells to generate immune stimulating or anti-cancer exosomes to produce a population of genetically engineered treatment resistant circulating tumor cells;
(d) administering the genetically engineered treatment resistant circulating tumor cells to the cancer patient.

2. The method of claim 1, further comprising, either sequentially or simultaneously,
(a) harvesting exosomes from the population of treatment resistant circulating tumor cells to produce a population of isolated treatment resistant circulating tumor cell exosomes;
(b) incubating the population of isolated treatment resistant circulating tumor cell exosomes with dendritic cells to form a population of exosome-loaded dendritic cells; and
(c) infusing the population of exosome-loaded dendritic cells into the cancer patient.

3. The method of claim 1, wherein the population of isolated circulating tumor cells is extracted from a biological fluid, a fragmented tumor, a tumor suspension, a tissue suspension, a cell culture, an established cell line, or combinations thereof.

4. The method of claim 1, wherein extracting circulating tumor cells further comprises using a biological fluid filtration system, immunomagnetic separation, a system for identification and enumeration of circulating tumor cells from blood, immunoaffinity purification using antibodies, capture using aptamers, nanostructured surfaces for capture, size-based filtration, microfluidic separation, dielectrophoresis-based separation, or combinations thereof.

5. The method of claim 1, wherein the population of isolated circulating tumor cells is greater than about 1,000 cells.

6. The method of claim 1, wherein isolating the population of treatment resistant circulating tumor cells from the population of isolated circulating tumor cells further comprises:
exposing the population of isolated circulating tumor cells to anti-cancer agents for 1, or more days; and
measuring cell viability and or cell survival.

7. The method of claim 1, wherein the population of treatment resistant circulating tumor cells is isolated from the population of circulating tumor cells when one or more anti-cancer agents inhibit tumor cell growth, decrease cell viability, and/or decrease cell survival by about 50% or more when compared to a tumor cell whose growth, viability, and/or cell survival is inhibited or destroyed by one or more anti-cancer agents.

8. The method of claim 1, wherein the population of treatment resistant circulating tumor cells comprises circulating tumor cells that are chemo-resistive, targeted therapy resistive, immunotherapy resistive, or cells resistant to combinations of treatments.

9. A method of treating a cancer patient comprising:

(a) extracting circulating tumor cells from a cancer patient to produce a population of isolated circulating tumor cells;

(b) isolating a population of treatment resistant circulating tumor cells from the population of isolated circulating tumor cells;

(c) harvesting exosomes from the population of isolated treatment resistant circulating tumor cells to produce a population of isolated treatment resistant circulating tumor cell exosomes;

(d) incubating the population of isolated treatment resistant circulating tumor cell exosomes with dendritic cells to form a population of exosome-loaded dendritic cells; and (e) infusing the population of exosome-loaded dendritic cells into a cancer patient in need thereof.

10. The method of claim 9, further comprising:

(f) genetically engineering the treatment resistant circulating tumor cells to generate immune stimulating or anti-cancer exosomes to produce a population of genetically engineered treatment resistant circulating tumor cells; and (g) administering the genetically engineered treatment resistant circulating tumor cells to the cancer patient in need thereof.

11. The method of claim 10, wherein (g) administering the genetically engineered treatment resistant circulating tumor cells to the cancer patient occurs simultaneously with (e) administering the population of exosome-loaded dendritic cells to the cancer patient in need thereof.

12. The method of claim 10, wherein (g) administering the genetically engineered treatment resistant circulating tumor cells to the cancer patient occurs prior to (e) infusing the population of exosome-loaded dendritic cells into the cancer patient in need thereof.

13. The method of claim 10, wherein (g) administering the genetically engineered treatment resistant circulating tumor cells to the cancer patient occurs after to (e) infusing the population of exosome-loaded dendritic cells into the cancer patient in need thereof.

14. The method of claim 10, wherein (g) administering the genetically engineered treatment resistant circulating tumor cells to the cancer patient and (e) infusing the population of exosome-loaded dendritic cells into the cancer patient in need thereof are separated by 2 or more hours.

15. The method of claim 10, wherein steps (f)-(g) are repeated 2 or more times.

16. The method of claim 9, wherein the population of isolated circulating tumor cells is greater than about 1,000 cells.

17. The method of claim 9, wherein the cancer patient and the cancer patient in need thereof are different patients.

18. The method of claim 9, wherein the cancer patient and the cancer patient in need thereof are the same patient.

19. The method of claim 9, wherein steps (a)-(e) are repeated 2 or more times.

20. The method of claim 9, wherein administering the population of exosome-loaded dendritic cells produces a localized response in the cancer patient in need thereof.

* * * * *